(12) United States Patent
Arora et al.

(10) Patent No.: US 8,435,924 B2
(45) Date of Patent: May 7, 2013

(54) METHOD OF PRODUCING COLOR CHANGE IN OVERLAPPING LAYERS

(75) Inventors: Kelyn Anne Arora, Cincinnati, OH (US); John Lee Hammons, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 555 days.

(21) Appl. No.: 12/611,965

(22) Filed: Nov. 4, 2009

(65) Prior Publication Data

US 2011/0104459 A1   May 5, 2011

(51) Int. Cl.
*B41M 5/34* (2006.01)

(52) U.S. Cl.
USPC .................. 503/201; 430/270.1; 604/385.01

(58) Field of Classification Search .............. None
See application file for complete search history.

(56) References Cited

U.S. PATENT DOCUMENTS

| | | | |
|---|---|---|---|
| 4,705,742 A | 11/1987 | Lewis | |
| 4,826,550 A | 5/1989 | Shimizu et al. | |
| 5,197,958 A | 3/1993 | Howell | |
| 5,210,064 A * | 5/1993 | Shon Baker et al. | 503/201 |
| 5,338,504 A | 8/1994 | Wang et al. | |
| 5,503,076 A | 4/1996 | Yeo | |
| 5,691,271 A * | 11/1997 | Yanagihara et al. | 503/204 |
| 5,710,094 A | 1/1998 | Minami et al. | |
| 5,730,961 A | 3/1998 | Goudjil | |
| 5,968,025 A | 10/1999 | Roe et al. | |
| 5,977,019 A * | 11/1999 | Ozeki et al. | 503/204 |
| 6,080,415 A | 6/2000 | Simon | |
| 6,092,002 A | 7/2000 | Kastman et al. | |
| 6,197,724 B1 * | 3/2001 | Aono | 503/209 |
| 6,306,409 B1 | 10/2001 | Ogawa | |
| 6,596,669 B1 | 7/2003 | Maruyama et al. | |
| 6,710,221 B1 | 3/2004 | Pierce et al. | |
| 6,719,742 B1 | 4/2004 | McCormack et al. | |
| 6,911,022 B2 | 6/2005 | Steger et al. | |
| 6,984,770 B2 | 1/2006 | Graeme, III et al. | |
| 7,306,582 B2 | 12/2007 | Adams et al. | |
| 7,311,696 B2 | 12/2007 | Christon et al. | |
| 7,402,157 B2 | 7/2008 | Christon et al. | |

(Continued)

FOREIGN PATENT DOCUMENTS

| EP | 0934737 A1 | 8/1999 |
|---|---|---|
| JP | 2001123088 | 5/2001 |

(Continued)

OTHER PUBLICATIONS

U.S. Appl. No. 12/766,730, filed Apr. 23, 2010, Kelyn Anne Arora et al.

(Continued)

*Primary Examiner* — Bruce H Hess
(74) *Attorney, Agent, or Firm* — Melody A. Jones; Jay A. Krebs (57) ABSTRACT

The present invention relates to methods of producing color change in overlapping layers of material. The method comprises providing a first layer having a first activatable colorant and a second layer having a second activatable colorant. A first external stimulus is applied to activate the first activatable colorant and produce a first activated color region in the first layer. A second external stimulus is applied to activate second activatable colorant and produce a second activated color region in the second layer.

12 Claims, 2 Drawing Sheets

U.S. PATENT DOCUMENTS

| | | |
|---|---|---|
| 7,485,403 B2 | 2/2009 | Khan |
| 2002/0062115 A1 | 5/2002 | Wada et al. |
| 2003/0109839 A1 | 6/2003 | Costea et al. |
| 2004/0170813 A1 | 9/2004 | Digiacomantonia et al. |
| 2005/0170726 A1 | 8/2005 | Brunson et al. |
| 2005/0256479 A1 | 11/2005 | Carlucci et al. |
| 2006/0021536 A1 | 2/2006 | Song et al. |
| 2006/0025735 A1 | 2/2006 | Berg, Jr. et al. |
| 2006/0025736 A1 | 2/2006 | Berg, Jr. et al. |
| 2006/0025737 A1 | 2/2006 | Song et al. |
| 2006/0072429 A1 | 4/2006 | Nagai et al. |
| 2006/0089071 A1 | 4/2006 | Leidig et al. |
| 2006/0246802 A1 | 11/2006 | Hughes et al. |
| 2007/0154687 A1 | 7/2007 | Luthi et al. |
| 2007/0156106 A1 | 7/2007 | Klofta et al. |
| 2008/0091162 A1 | 4/2008 | Maldonado et al. |
| 2008/0132865 A1 | 6/2008 | Li et al. |
| 2008/0195072 A1 | 8/2008 | Warner |
| 2008/0206529 A1 | 8/2008 | Veminami et al. |
| 2008/0228157 A1 | 9/2008 | McKiernan et al. |
| 2008/0233379 A1 | 9/2008 | O'Connor |
| 2008/0234644 A1 | 9/2008 | Hansson et al. |
| 2008/0269704 A1 | 10/2008 | Hansson et al. |
| 2008/0277621 A1 | 11/2008 | MacDonald et al. |
| 2008/0279253 A1 | 11/2008 | MacDonald et al. |
| 2008/0287903 A1 | 11/2008 | Vega et al. |
| 2008/0305328 A1 | 12/2008 | Green et al. |
| 2009/0030390 A1 | 1/2009 | Hammons et al. |
| 2009/0058892 A1 | 3/2009 | VanDemark |
| 2009/0191476 A1 | 7/2009 | Rogers et al. |
| 2009/0191480 A1 | 7/2009 | Rogers et al. |

FOREIGN PATENT DOCUMENTS

| | | |
|---|---|---|
| JP | 2002138322 | 5/2002 |
| JP | 2003/199791 A | 7/2003 |
| JP | 2007/050145 A | 3/2007 |
| WO | WO-2006/018640 | 2/2006 |
| WO | WO-2006/114600 A3 | 5/2007 |
| WO | WO-2009/093028 A2 | 7/2009 |
| WO | WO-2011/025486 A1 | 3/2011 |

OTHER PUBLICATIONS

U.S. Appl. No. 12/766,705, filed Apr. 23, 2010, Kelyn Anne Arora et al.

U.S. Appl. No. 12/766,716, filed Apr. 23, 2010, Kelyn Anne Arora et al.

U.S. Appl. No. 12/611,962, filed Nov. 4, 2009, Kelyn Anne Arora et al.

U.S. Appl. No. 12/766,698, filed Apr. 23, 2010, Kelyn Anne Arora et al.

International Search Report dated Apr. 14, 2011, 5 pages.

International Search Report dated Dec. 9, 2010, 7 pages.

\* cited by examiner

METHOD OF PRODUCING COLOR CHANGE IN OVERLAPPING LAYERS

FIELD OF THE INVENTION

The present invention is related to activatable colorants that are activated to produce color. Specifically, the invention is related to a method of producing colored regions in overlapping layers of material by activating activatable colorants in the overlapping layers.

BACKGROUND OF THE INVENTION

A variety of absorbent articles that include different colored regions are available in the to market. Absorbent articles such as sanitary napkins and female adult incontinence articles that function to collect fluid discharged from a woman's vagina or urethra sometimes include a colored region proximal the central portion of the absorbent article that differs in color from portions of the absorbent article remote from the central portion of the absorbent article. Absorbent articles such as sanitary napkins have also been known to include decorative designs on the topsheet and backsheet that are appealing to consumers. However, absorbent articles currently available in the market place are generally provided with colored regions on only a single component, such as the secondary topsheet or topsheet or backsheet. One reason for limiting the colored regions to such single components is the difficulties associated with registering colored regions disposed on multiple components during manufacturing. Nevertheless, limiting colored regions to a single component or layer limits the design space in which designers can create innovative designs that meet consumer demands.

High speed manufacturing lines that include printing capability represent a high capital cost to manufacturers of absorbent articles. For manufacturers to effectively recover the cost of such capital, it is advantageous for manufactures to use existing manufacturing lines to continue manufacturing absorbent articles. In some instances, the approach manufacturers have chosen to provide for colored regions might not be easily adapted to provide for colored regions that are disposed on multiple components or layers due to the crowded nature of the manufacturing line. Thus, if a manufacturer desires to provide for visual elements on multiple components of the absorbent article, the manufacturer might have to retool the manufacturing line to provide for additional printing and registration capabilities, thus incurring additional capital cost.

With these limitations in mind, there is a continuing unaddressed need for absorbent articles that can be manufactured cost effectively using existing manufacturing capability that can be provided with colored regions on multiple layers so that designers have a richer palette of color impression with which to work. Still further there is a need for providing absorbent articles with colored regions on multiple layers without requiring additional printing capabilities for printing on multiple layers or registration capabilities for registering the colored regions on multiple layers during manufacturing.

SUMMARY OF THE INVENTION

Methods of producing color change in overlapping layers of material are disclosed. The methods comprise providing a first layer having a first activatable colorant and a second layer having a second activatable colorant. A first external stimulus is applied to the overlapping layers to activate the first activatable colorant and produce a first activated color region in the first layer. A second external stimulus is applied to the overlapping layers to activate the second activatable colorant and produce a second activated color region in the second layer. The first and second activatable colorants are selected from at least one of thermochromic material, photoreactive material and piezochromic material. The types of external stimuli include temperature, electromagnetic radiation, and pressure. The external stimulus for each activatable colorant can be applied simultaneously or in sequence producing colors on the first and second layers that are visible from outside the layers. The first and second overlapping layers include films, nonwovens, air laids, fibers, filaments, adhesives, lotions, absorbent gelling materials, thermoplastic polymers and foams.

In one embodiment, the external stimulus for the first activatable colorant comprises electromagnetic radiation and the external stimulus for the second activatable colorant is selected from at least one of change of temperature, electromagnetic radiation, and pressure. In another embodiment, the external stimulus for the first and second activatable colorants comprises electromagnetic radiation. In still another embodiment, the electromagnetic radiation comprises UV light.

In an alternate embodiment, the method of producing color change in overlapping layers comprises providing a first web layer having a first activatable colorant and applying a first external stimulus to activate the first activatable colorant and produce a first activated color region in the first web layer. A second web layer is provided having a second activatable colorant. A second external stimulus is applied to activate the second activatable colorant and produce a second activated color region in the second web layer. The first and second web layers are combined such that the second web layer overlaps the first web layer.

In another alternate embodiment, the method of producing color change in overlapping layers comprises providing a first layer having a first activatable colorant and applying a first external stimulus to activate the first activatable colorant and produce a first activated color region in the first web layer. A second layer is provided having a second activatable colorant wherein the second layer overlaps the first layer. A second external stimulus is applied to the overlapping layers to activate the second activatable colorant and produce a second activated color region in the second layer.

DETAILED DESCRIPTION OF THE INVENTION

Definitions

As used herein and in the claims, the term "comprising" is inclusive or open-ended and does not exclude additional unrecited elements, compositional components, or method steps.

As used herein, "machine direction" means the path that material, such as a web, follows through a manufacturing process.

As used herein "cross direction" means the path that is perpendicular to the machine direction in the plane of the web.

"Absorbent article" means devices that absorb and/or contain liquid. Wearable absorbent articles are absorbent articles placed against or in proximity to the body of the wearer to absorb and contain various exudates discharged from the body. Nonlimiting examples of wearable absorbent articles include diapers, pant-like or pull-on diapers, training pants, sanitary napkins, tampons, panty liners, incontinence devices, and the like. For the purpose of this invention, the term "absorbent article" not only includes the wearable portion of the article but also packaging for individual articles such as release paper wrappers (RPW) and applicators such as tampon applicators. Additional absorbent articles include wipes and cleaning products.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, airlaid, and bonded carded web processes, including carded thermal bonding. The basis weight of nonwoven fabrics is usually expressed in grams per square meter (g/m2). The basis weight of a laminate web is the combined basis weight of the constituent layers and any other added components. Fiber diameters are usually expressed in microns; fiber size can also be expressed in denier, which is a unit of weight per length of fiber. The basis weight of laminate webs suitable for use in the present invention can range from 6 g/m2 to 400 g/m2, depending on the ultimate use of the web. For use as a hand towel, for example, both a first web and a second web can be a nonwoven web having a basis weight of between 18 g/m2 and 500 g/m2.

As used herein, "spunbond fibers" refers to relatively small diameter fibers which are formed by extruding molten thermoplastic material as filaments from a plurality of fine, usually circular capillaries of a spinneret with the diameter of the extruded filaments then being rapidly reduced by an externally applied force. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky; to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross sectional area of the fiber and the various polymers are usually not continuous along the entire length of the fiber, instead usually forming fibers which start and end at random. Biconstituent fibers are sometimes also referred to as multi-constituent fibers.

As used herein, the term "non-round fibers" describes fibers having a non-round cross-section, and include "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET polyester).

As used herein, the term "overlapping layers" describes two or more materials that extend over or cover one another, entirely or in part. The overlapping layers can comprise adjacent face to face overlapping layers or non adjacent layers with a layer having no activatable colorant disposed in between.

"Laminate" means two or more materials that are bonded to one another by methods known in the art, e.g. adhesive bonding, thermal bonding, ultrasonic bonding, extrusion lamination.

As used herein, the term "tampon" refers to any type of absorbent structure such as, e.g., an absorbent mass, that can be inserted into the vaginal canal or other body cavity, such as, e.g., for the absorption of fluid therefrom, to aid in wound healing, and/or for the delivery of materials, such as moisture or active materials such as medicaments. In general, the term "tampon" is used to refer to a finished tampon after the compression and/or shaping process.

As used herein, the term "pledget" refers to an absorbent material prior to the compression and/or shaping of the material into a tampon. Pledgets are sometimes referred to as tampon blanks or softwinds.

As used herein, the term "applicator" refers to a device or implement that facilitates the insertion of a feminine hygiene product, such as, e.g., a tampon or pessary, into an external orifice of a mammal. Suitable applicators include, e.g., telescoping, tube and plunger, and to compact applicators.

The term "color" as referred to herein includes any primary color, i.e., white, black, red, blue, violet, orange, yellow, green, and indigo as well as any declination thereof or mixture thereof. The term 'non-color' or 'non-colored' refers to the color white which is further defined as those colors having an L* value of at least 90, an a* value equal to 0±2, and a b* value equal to 0±2.

"Color change" herein means that at least a part of layer including an activatable colorant changes its color in response to an external stimulus. The change in color is visible from outside the layer. A change in color "visible from outside the layer" as used herein means that the color change is detectable by the naked human eye.

"Activatable colorant" means a material which provides the color change in response to an external stimulus.

"External stimulus" means the exposure of the absorbent article to energy from outside the article in the form of pressure, temperature, light or combinations thereof.

"Activated color region" means areas containing a colorant that has been activated by external stimulus.

"Visible" means those colors and wavelengths of light that are detectable by the human eye, nominally about 400-700 nanometers in wavelength.

"Electromagnetic radiation" means those areas of the spectrum amenable to industrial applications, such as the ultraviolet through the infrared wavelengths "Activatable chemistry" means those chemicals, monomers and polymers which are capable of being affected by an external stimulus.

"Disposable" means absorbent articles that are not intended to be launched or otherwise restored or reused as absorbent articles (i.e., they are intended to be discarded after a single use and, preferably to be recycled, composted or otherwise disposed of in an environmentally compatible manner).

As used herein, "hot-melt adhesive" refers to a thermoplastic polymer composition that is heated to obtain a liquid of flowable viscosity, and after application to an adherend, cooled to obtain a solid. An adhesive bond is formed when the adhesive solidifies upon cooling to a temperature below its melt temperature or below its solidification transition temperature.

Regarding all numerical ranges disclosed herein, it should be understood that every maximum numerical limitation given throughout this specification includes every lower numerical limitation, as if such lower numerical limitations were expressly written herein. In addition, every minimum numerical limitation given throughout this specification will include every higher numerical limitation, as if such higher numerical limitations were expressly written herein. Further, every numerical range given throughout this specification will include every narrower numerical range that falls within such broader numerical range and will also encompass each individual number within the numerical range, as if such narrower numerical ranges and individual numbers were all expressly written herein.

The present invention provides two or more overlapping layers containing activatable colorants that change color when exposed to an external stimulus. The overlapping layers comprise a first layer comprising a first activatable colorant and a second layer comprising a second activatable colorant. The first and second layers containing the activatable colorant and forming the overlapping layers can comprise adjacent face to face overlapping layers or non adjacent layers with a layer having no activatable colorant disposed in between. The activatable colorant can be disposed throughout a layer or limited to only a portion of the layer (e.g. in one component of multicomponent fibers or in one or more layers of multilayer film). The first and second layers can be sized such that the second layer completely overlaps the first layer. Alternatively the second layer can be smaller than the first layer such that the second layer partially overlaps the first layer. In alternate embodiments, one or both the first and second layers can comprise translucent layers such as films or non translucent layers such as nonwovens and coatings. In addition, one or both the first and second layers can include apertures.

Once activated by an external stimulus, the activatable colorants form activated color regions in the overlapping layers. The activated color regions can comprise uniform colored regions covering large sections or entire areas of the overlapping layers or nonuniform colored regions comprising varying patterns of colored regions on each of the overlapping layers. Alternatively, the activated color regions can include multiple color patterns, zone patterns and multiple shades of a single color. The activatable colorants can also be activated to form activated color regions comprising written text, graphics, and intricate artwork.

The activatable colorant can produce a color change that is reversible or irreversible. However, preferably the activatable colorant according to the present invention produces a color change that is irreversible, thereby providing a permanent visual effect. Sources of activatable colorants include 'thermochromic', which means that the color change is induced by a change of temperature, or 'photoreactive', which means that the color change is induced by electromagnetic radiation, or 'piezochromic', which means that the color change is induced by pressure. Each of these sources of activatable colorants is discussed more fully below.

The overlapping layers according to the present invention include films, nonwovens, air laids, fibers, filaments, adhesives, lotions, absorbent gelling materials and foams. The composition used to form the overlapping layers of the present invention, particularly films and nonwovens, can include thermoplastic polymeric and non-thermoplastic polymeric materials. For fibers and nonwovens, thermoplastic polymeric material used in forming fibers must have rheological characteristics suitable for melt spinning. The molecular weight of the polymer must be sufficient to enable entanglement between polymer molecules and yet low enough to be melt spinnable. For melt spinning, thermoplastic polymers have molecular weights below about 1,000,000 g/mol, preferably from about 5,000 g/mol to about 750,000 g/mol, more preferably from about 10,000 g/mol to about 500,000 g/mol and even more preferably from about 50,000 g/mol to about 400,000 g/mol. Unless specified elsewhere, the molecular weight indicated is the number average molecular weight.

The thermoplastic polymeric materials are able to solidify relatively rapidly, preferably under extensional flow, and form a thermally stable fiber structure, as typically encountered in known processes such as a spin draw process for staple fibers or a spunbond continuous fiber process. Preferred polymeric materials include, but are not limited to, polypropylene and polypropylene copolymers, polyethylene and polyethylene copolymers, polyester and polyester copolymers, polyamide, polyimide, polylactic acid, polyhydroxyalkanoate, polyvinyl alcohol, ethylene vinyl alcohol, polyacrylates, and copolymers thereof and mixtures thereof. Other suitable polymeric materials include thermoplastic starch compositions as described in detail in U.S. publications 2003/0109605A1 and 2003/0091803. Other suitable polymeric materials include ethylene acrylic acid, polyolefin carboxylic acid copolymers, and combinations thereof. Other suitable polymeric materials comprising starch and polymers are described in U.S. Pat. No. 6,746,766, U.S. Pat. No. 6,818, 295, U.S. Pat. No. 6,946,506 and U.S. application Ser. No. 03/0092343. Common thermoplastic polymer fiber grade materials are preferred, most notably polyester based resins, polypropylene based resins, polylactic acid based resin, polyhydroxyalkonoate based resin, and polyethylene based resin and combination thereof. Most preferred are polyester and polypropylene based resins.

The overlapping layers according to the present invention can include an adhesive having an activated colorant incorporated in a component forming the adhesive. The adhesive can provide one of the two overlapping layers as a coating. Alternatively, the adhesive can be incorporated into a layer such as a nonwoven forming one of the two overlapping layers. Such an adhesive can comprise a hot melt adhesive.

Hot-melt adhesives used as construction adhesives in the manufacture of disposable absorbent articles typically include several components. These components include one or more polymers to provide cohesive strength, such as ethylene-vinyl acetate, copolymers, polypropylene, phenoxy resins, styrene-butadiene copolymers, ethylene-ethyl acrylate copolymers, low density polypropylenes, polyesters, polyamides, and polyurethanes. These polymers make up a significant part of the hot-melt adhesive composition. The composition also includes components such as, for example, a resin or analogous material (sometimes called a tackifier) to provide adhesive strength. Examples of such materials include hydrocarbons distilled from petroleum distillates, rosins and/or rosin esters, and terpenes derived, for example, from wood or citrus. The composition also typically includes waxes, plasticizers or other materials to modify viscosity. Examples of such materials include mineral oil, polybutene, paraffin oils, ester oils, and the like. Still further, the composition can optionally include additives, such as antioxidants or other stabilizers. A typical hot-melt adhesive composition might contain from about 15 to about 35 weight percent (wt. %) cohesive strength polymer(s); from about 50 to about 65 wt. % resin or other tackifier(s); from more than zero to about 30 wt. % plasticizer or other viscosity modifier; and optionally less than about 1 wt. % stabilizer or other additive.

In an alternate embodiment, activatable colorant can be included as an additive in a lotion that is applied to a layer. Disposable absorbent articles, such as diapers, training pants, and catamenial devices having lotion topsheets are known. By including an activated colorant in a lotion that is applied to a topsheet, the activated color regions can identify the areas where lotion is present. For this embodiment, a first layer comprising a first activatable colorant may comprise a substrate forming a topsheet and the second layer comprising the second activatable colorant can comprise the lotion overlapping the first layer in the form of coating. Alternatively, for this embodiment, the second layer can comprise a second substrate incorporating a lotion containing the second activatable colorant forming a lotioned primary topsheet which overlaps a first layer comprising a first substrate containing a first activatable colorant which forms a secondary topsheet.

Lotions of various types are known to provide various skin benefits, such as prevention or treatment of diaper rash as disclosed in U.S. Pat. No. 6,861,571 issued to Roe, et al, U.S. Pat. No. 5,607,760 issued to Roe and U.S. Pat. No. 5,643,588 issued to Roe, et al. Such lotion compositions comprise (1) an emollient(s); (2) an immobilizing agent(s); (3) optionally a hydrophilic surfactant(s); and (4) other optional components. These lotions can be applied to the to topsheet of absorbent articles, for example, and can be transferred to the skin of the wearer during use. For instance, when applied to the outer surface of a diaper topsheets, the lotion compositions can be transferable to the wearer's skin by normal contact, wearer motion, and/or body heat. Activatable colorants can be incorporated into the lotion, applied to a topsheet and subsequently activated to produce activated colored region.

In preparing lotioned absorbent articles according to the present invention, the lotion composition including activatable colorant can be applied to the outer surface (i.e., body facing surface) of the topsheet, but can also be applied to the inner surface of the topsheet or to any other component of the absorbent article. Any of a variety of application methods that evenly distribute the lotion composition can be used. Suitable methods include spraying, printing (e.g., flexographic printing), coating (e.g., gravure coating), extrusion, or combinations of these application techniques, e.g. spraying the lotion composition on a rotating surface, such as a calender roll, that then transfers the composition to the outer surface of the topsheet. Lotion compositions of the present invention can be applied by printing methods, or continuous spray or extrusion as is known in the art, or as is described in U.S. Pat. No. 5,968,025.

The lotion composition may be applied to the entire surface of the topsheet or portions thereof. The lotion composition can be applied in a stripe aligned with and centered on the longitudinal centerline of the disposable absorbent article. The lotion composition can be applied in a plurality of stripes having uniform or non-uniform widths. Alternatively the lotion can be aligned with and centered in opposition to the longitudinal centerline. It can be preferred that the lotion be applied in a plurality of stripes parallel to the longitudinal axis of the absorbent article. This allows for both transfer of the lotion to a broader area of the vulva and improved fluid handling of the absorbent article.

Alternatively, the lotion composition can also be applied nonuniformly to the outer surface of the topsheet. By "nonuniformly" is meant that the amount, pattern of distribution, etc. of the lotion composition can vary over the topsheet surface. For example, some portions of the treated surface of the topsheet can have greater or lesser amounts of lotion composition, including portions of the surface that do not have any lotion composition on it. For example, the lotion composition can be applied on one region of the topsheet in the shape of a rectangle and/or a circle, and/or as multiplicity of dots.

For each of the aforementioned embodiments, the activatable colorant is blended into or coated onto material forming a layer. The activatable colorants are subsequently activated to change its color by inputs such as electromagnetic radiation (exposure to broad spectrum light, including ultraviolet, visible and infrared, etc.) temperature or pressure. Although the activation can occur on individual layers prior to assemblage, the activation preferably occurs after the overlapping layers are put together in order to avoid having to register the color patterns during assembly. The activatable colorant disposed on or within each overlapping layer can be activated individually in sequence; however, preferably the activatable colorants disposed on the overlapping layers are activated simultaneously.

Overlapping layers according to the present invention can comprise the same type of activatable colorant or different types of activatable colorants. However, preferably at least one of the overlapping layers comprises an activatable colorant comprising a photoreactive material. For instance, the activatable colorant on the first layer and the second layer can comprise a photoreactive material. Alternatively, the activatable colorant on the first layer can comprise a photoreactive material while the activatable colorant on the second overlapping layer comprises either a thermochromic material or a piezochromic material.

Alternate embodiments also include overlapping layers having two or more different activatable colorants in a single layer. For instance a single layer may include a photoreactive material and a thermochromic material and/or a piezochromic material. Alternatively, a single layer may include two or more activatable colorants that are the same type but have different chemistries. For instance, two photoreactive materials having different chemistries may be disposed in a single layer.

Color Change Material

As briefly described above, the color change material can be 'thermochromic', which means that the color change is induced by a change of temperature, or 'photoreactive', which means that the color change is induced by electromagnetic radiation, or 'piezochromic', which means that the color change is induced by pressure. These definitions comprise materials changing color irreversibly, reversibly or quasi-reversibly in response to the respective stimulus. Thermochromic materials herein also comprise pseudo-thermochromic materials showing a hysteresis of thermochromism. Combinations of the aforementioned mechanisms in the color change material are also within the scope of the present invention. The color change materials herein can either be coated onto parts of the absorbent article, such as on films or fibers, or can to form an integral part of components of the absorbent article by being added e.g. to the polymeric master batch these components are made of. The color change materials herein change their color in response to external stimuli as defined hereinbefore.

a) Thermochromic Materials

Thermochromic pigments are organic compounds that effectuate a reversible or irreversible color change when a specific temperature threshold is crossed. A thermochromic pigment may comprise three main components: (i) an electron donating coloring organic compound, (ii) an electron accepting compound and (iii) a solvent reaction medium determining the temperature for the coloring reaction to occur. One example of a commercially available, reversible thermochromic pigment is 'ChromaZone® Thermobatch Concentrates available from Thermographic Measurements Co. Ltd. Thermochromic pigments and the mechanism bringing about the temperature triggered color change are well-known in the art and are for example described in U.S. Pat. No. 4,826,550 and U.S. Pat. No. 5,197,958. Other examples of thermochromic pigments are described in published US application 2008/0234644A1.

Thermochromic or temperature sensitive color changing fibers are known from the textile field to be used in clothing, sport equipment, etc. The fibers are either produced by blending a thermochromic pigment in the base resin from which the fibers are to be produced, for example a polyolefin, such as polyethylene or polypropylene, polyester, polyvinyl alcohol etc. or by using a thermochromic coloring liquid for the fibers. The production of temperature sensitive color-changing fibers are disclosed in for example JP2002138322 and JP2001123088. The fibers change color at a selected temperature. The change of color is either reversible or irreversible.

An example of a fiber which can be used according to the invention is a thermochromic fiber which is partly characterized in that the flexural modulus of elasticity of a base resin is within the range of 300-1,500 MPa in the temperature-sensing color-changing fiber. The fiber is formed by melt blending a thermally color-changing pigment in a dispersed state in the base resin of a polyolefin resin and/or the polyolefin resin blended with a thermoplastic resin. The fiber is further described in JP 2002-138322.

Alternatively, the thermosensitive pigment may be of a microcapsule type which is known in the art of thermosensitive pigments.

b) Piezochromic Materials

Any piezochromic materials disclosed in the art are suitable herein as long as they meet the necessary health and safety requirements. An example is disclosed in U.S. Pat. No. 6,330,730.

In one example the piezochromic material is thermochromic and responds to a temperature increase caused by applied pressure. In another example the piezochromic material comprises a dye, which is encapsulated into microcapsules. Upon application of pressure these capsules break and release the dye, which then becomes visible. The color intensity is directly linked to the amount of pressure applied. Typical piezochromic materials require a pressure of from 14 to 140 kPa.

Most typically piezochromic color change materials change their color in an irreversible fashion after exertion of pressure. This is due to the fact that the color change was achieved by the destruction of microcapsules, in which the substances for achieving the color change were encapsulated.

c) Photoreactive Materials

Photoreactive materials change color in response to exposure to electromagnetic radiation. The color change can be irreversible providing a permanent change in color or it can be reversible providing a temporary change in color.

Photochromic materials are those that reversibly change color when exposed to light or changes in light intensity. Photochromic materials typically provide a reversible color change transiting from a colorless state to a color state upon exposure to light and back to a colorless state when reversed. Examples for photochromic materials are described in U.S. Pat. No. 6,306,409; U.S. Pat. No. 6,080,415 or U.S. Pat. No. 5,730,961.

Polychromic materials are those which are capable of generating multiple colors. Compounds based upon diacetylene, when polymerized, are known to take on different color properties. Polymerization is typically achieved by exposure to certain types of radiation, such as ultraviolet radiation. Varying the intensity of the radiation causes differing degrees of polymerization, and different colors.

It is known that these properties can be utilized to achieve multi-color printing. See, for example; U.S. Pat. No. 4,705,742, "Processless Multicolour Imaging", issued on Nov. 10, 1987, assigned to Gaf Corporation; and WO2006/018640, "Multi-colour printing", published on Feb. 23, 2006, Sherwood Technologies Ltd. Both of these documents disclose methods of applying coatings comprising various diacetylene compounds to the surface of a substrate for the purpose of irradiating and forming an image on the surface of the substrate.

Particularly preferred materials are those that can be dispersed or blended into the polymeric matrix of the layers, such as those disclosed in PCT publication WO 2009/093028A2 and WO 2009/081385 A2, which are compounds which undergo a color change upon irradiation, and which have the general structure: X—C≡C—C≡C—Y—(CO)n-QZ wherein X is H, alkyl or —Y—(CO)n-QW; each Y is the same or a different divalent alkylene group; Q is O, S or NR; R is H or alkyl; W is H, alkyl or Z; each Z is the same or a different unsaturated alkyl group; and each n is 0 or 1.

Another example of a material of use in the present invention is a thermoplastic material comprising polymer mixed with a charge transfer agent and a photo acid generating agent such as those described in US 2009/0191476A1. Exposure of the thermoplastic material comprising the charge transfer agent and photo acid generating agent to irradiation will bring about a color change reaction which can be used to create text, artwork, devices or other images and effects.

Absorbent articles according to the present invention preferably comprise photoreactive materials providing an irreversible, permanent change in color. Examples of photoreactive materials providing permanent color change are described in PCT publication WO 2009093028A2 which describes polychromic substances comprising diacetylene compounds that change color when subjected to irradiation. The type of radiation that performs the color change reaction with the diacetylene compounds includes laser or non-coherent, broadband or monochromatic radiation. Specific radiation types include ultraviolet, near, mid or far infrared, visible, microwave, gamma ray, x-ray or electron beam.

Ultraviolet irradiation is preferred for changing substrates comprising the diacetylene compounds from colorless or low visual color to color on exposure to ultraviolet irradiation, and then change to a color different to the first on subsequent exposure to infrared irradiation. Laser irradiation may be preferred for writing text and drawing intricate artwork directly on substrates comprising the diacetylene compounds, as laser imaging can be conveniently controlled by computer with the appropriate software and has superior resolution capability. However, similar effects can be obtained by passing radiation from, for example, an ultraviolet lamp through a mask before it reaches the substrates comprising the diacetylene compound.

Another application describing of photoreactive materials providing permanent color change includes WO 2009/081385 which describes thermoplastic material comprising polychromic substance wherein the polychromic substance is a functionalized diacetylene having a formula which has a general structure that is described therein.

Activation of photoreactive materials is preferably achieved using an ultraviolet lamp. One example is the Coil Clean (CC) Series ultraviolet fixtures available from American Ultraviolet (Lebanon, Ind.). Another UVC exposure unit suitable for use in activation of photoreactive materials consists of a metal enclosure containing 8 UV amalgam lamps and 8 ballasts with individual circuits for individual lamp controls and a fan for cooling lamps to maintain temperature. The lamps are 357 mm in length and are available from American Ultraviolet as part number GML750A.

Other examples of equipment that may be used for activation of photoreactive materials include the J3825 MonoCure Lamphead from Nordson UV Limited (Berkshire UK) and the 270S UV Lamp Assembly and Power Supply by Integrated Technology. The type of lamp within the unit may be changed to vary the spectral output as needed. Examples of relevant bulb types include "H", "V", "D" and "Q".

The overlapping layers having activatable colorants according to the present invention is applicable, but not limited to absorbent articles such as diapers, sanitary napkins, tampons, panty liners, incontinence devices, wipes and the like. For absorbent articles, the first and second overlapping layers having activatable colorants can include topsheets, secondary topsheets, acquisition layers absorbent cores and backsheets. Alternatively, the overlapping layers can be applicable to various components of the absorbent article such as fasteners, barrier cuffs, and landing zones. In addition, overlapping layers can include a first layer comprising a backsheet of an absorbent article and a second layer such as a release paper wrapper forming packaging for an individual article.

For illustrative purposes, the present invention will be described in terms of panty liners and sanitary napkins. Non-limiting examples of panty liners and sanitary napkins which may be provided with a first layer having a first activatable colorant and a second layer having a second activatable colorant include those manufactured by The Procter & Gamble Company of Cincinnati, Ohio, such as ALWAYS ULTRA, ALWAYS INFINITY, and ALWAYS pantiliners. Absorbent articles such as those disclosed in U.S. Pat. Nos. 4,324,246, 4,463,045, 6,004,893, 4,342,314, 4,463,045, 4,556,146, 4,589,876, 4,687,478, 4,950,264, 5,009,653, 5,267,992, and Re. 32,649 are also contemplated being absorbent articles that might benefit from such a structure. Other absorbent article embodiments including overlapping layers with activatable colorants can include a tampon and an applicator where the first layer comprises the tampon and the second overlapping layer comprises the applicator.

The generation of color change in overlapping layers in absorbent articles according to the present invention will be described with reference to the following figures which illustrate certain embodiments. It will be apparent to those skilled in the art that these embodiments do not represent the full scope of the invention which is broadly applicable in the form of variations and to equivalents as may be embraced by the claims appended hereto. For instance, the following description is in reference to a catamenial pad product; however, the present invention is equally applicable to a tampon and applicator combination. Furthermore, features described or illustrated as part of one embodiment may be used with another embodiment to yield still a further embodiment. It is intended that the scope of the claims extend to all such variations and equivalents. For instance the embodiment provided in description that follows includes overlapping web layers with activatable colorants forming a sanitary napkin. In an alternate embodiment the overlapping layers with the activatable colorants include a sanitary napkin backsheet and release paper wrapper (RPW) where the first layer comprises the backsheet and the second overlapping layer comprises the RPW.

Figure 1:
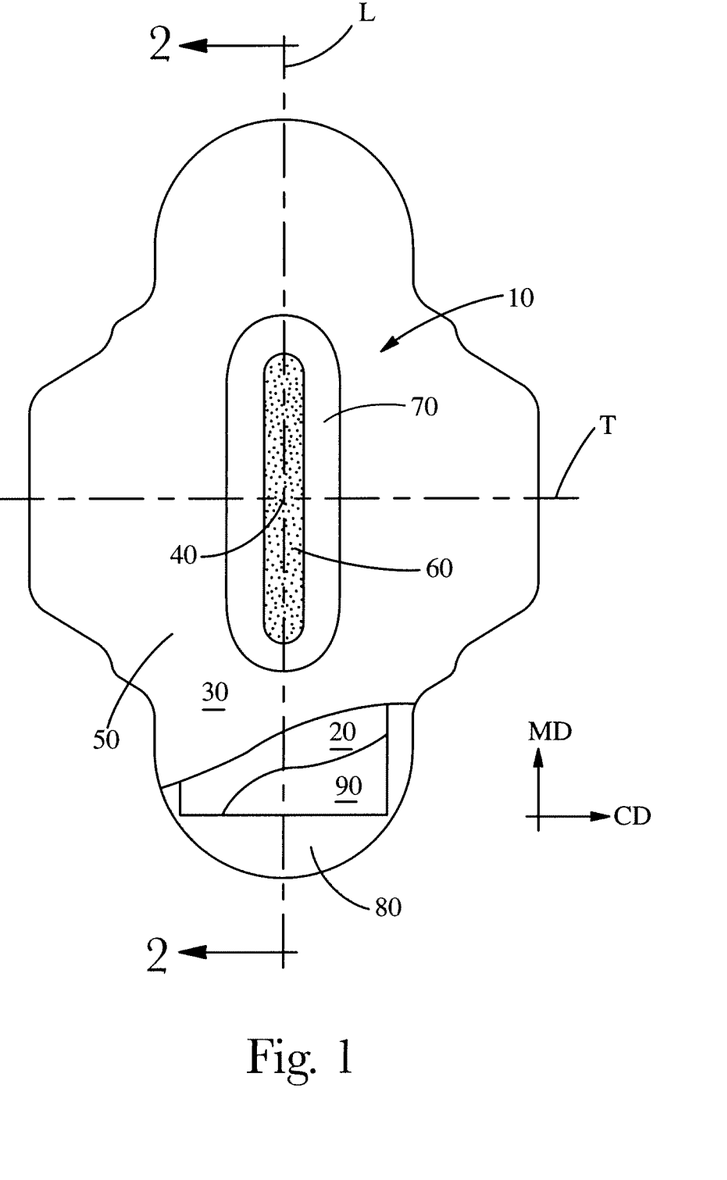
FIG. 1 is a schematic of an absorbent article.

A top view of an absorbent article 5 comprising a sanitary napkin is shown in FIG. 1. The absorbent article 5 can have a substantially planar configuration and a centroid 40. The centroid 40 can be the intersection between the longitudinal centerline L and transverse centerline T. The absorbent article 5 can have a body facing surface 10 and a garment facing surface. The absorbent article 5 can have a machine direction MD and a cross machine direction CD.

As shown in FIG. 1, the absorbent article 5 can be considered to have a viewing surface that is the body facing surface 10. The body facing surface 10 can be the side of the absorbent article 5 that is in contact with the wearer's body when the absorbent article 5 is worn, as might be the case for a sanitary napkin, panti-liner, or adult incontinence product, or is inserted into the wearer's body, as might be the case for a tampon.

For the absorbent article 5 comprising a sanitary napkin shown in FIG. 1, first layer 20 can function as an inner layer such as a secondary topsheet or insert and second layer 30 can function as a primary topsheet. Both the secondary topsheet and primary topsheet can comprise a fluid pervious polymer film, fluid pervious nonwoven or other suitably fluid pervious material. In another embodiment, a topsheet, such as a fluid pervious polymer film or fluid pervious nonwoven, can be between the wearer's body and the second layer 30. The first layer 20 and second layer 30 can be perceived by an observer when the body facing surface 10 is presented towards the observer even though the second layer 30 is between the observer and the first layer 20.

The absorbent article 5 can have a first activated colored region 60 and second activated colored region 70. The first activated colored region 60 and second activated colored region 70 can be viewable from the body facing surface 10.

When the body facing surface 10 of the to absorbent article 5 is viewed, the absorbent article 5 can have a background region 50. The background region 50 is a region that is visually distinguishable from the first activated colored region 60 and second activated colored region 70. The background region 50 can be white or any other color visually distinguishable from the first activated colored region 60 and second activated colored region 70. Colors are believed to be visually distinguishable if there is a ΔE between the two colors of at least about 1.

The first layer 20 comprises a first activatable colorant that is activated to create a first activated colored region 60. The first activated colored region 60 can be a constituent part of first layer 20, as might be the case if a predetermined portion of first layer 20 comprises fibers formed from polymers including the first activatable colorant or the first activatable colorant can be added to the first layer as a coating, adhesive or lotion, etc. The first activated colored region 60 can be provided on, for instance, the body facing side of the first layer 20 or the garment facing side of the first layer 20, the garment facing side being the side of the absorbent article oriented away from the wearer's body. The body facing side of the first layer 20 is oriented towards the second layer 30.

Similarly, the second layer 30 comprises the second activatable colorant which is activated to form a second activated color region 70. Similar to the first activatable colorant, the second activated colored region 70 can be a constituent part of second layer 30, as might be the case if a predetermined portion of second layer 30 comprises fibers formed from polymers including the second activatable colorant or the second activatable colorant can be added to the first layer as a coating, adhesive or lotion, etc. The second activated colored region 70 can be provided on, for instance, the body facing side of the second layer 30 or the garment facing side of the second layer 30, the garment facing side being the side of the absorbent article oriented away from the wearer's body and towards the first layer 20. Providing the first activated colored region 60 and the second activated colored region 70 on two different layers of material may provide for a manufacturing approach that does not require registration of the first and second activated colored regions when the first and second layers are assembled to produce the desired absorbent article 5. For instance, the first and second activatable colorants can be activated after the first and second layers 20, 30 are assembled to form the corresponding first and second activated color regions 60 and 70. Such color activation can occur in sequence or simultaneously.

The first and second activated color regions 60, 70 shown in FIG. 1 are concentric elongated ellipses, such that the first activated color region forms an inner elongated ellipse and the second activated color region forms an outer elongated ellipse. However, the first and second activated color regions 60, 70 can have numerous shapes and sizes. They can be open or filled circles or ellipses, or straight or bent lines, dots, squares or rectangles or the like. They can also comprise written text and artwork. The first and second activated color regions 60, 70 can extend across the whole length and/or width of the article or only across part thereof. It is also within the scope of the present invention that the activated color regions extend across the whole first layer 20 and/or second layer 30.

A second activated colored region 70 that is laterally more extensive than the first activated colored region 60 can provide the impression to the wearer that such laterally more extensive portions of the absorbent article 5 are capable of acquiring and retaining fluid. For instance, if the second activated colored region 70 extends across a substantial portion of the absorbent article 5 in the cross-direction CD, viewers of the absorbent article 5 may interpret the second activated colored region 70 as providing a barrier to fluid flow beyond such second activated colored region 70 or a boundary beyond which the wearer should not expect fluid to pass as the fluid travels in the machine-direction MD.

Colored regions of varying width activated on different layers of materials may also offer a wider array of design choices to designers for creating the impression of depth in the absorbent articles 5 and communicating various functions of portions of absorbent article 5, such as portions of the absorbent article that might act or be perceived to act as a barrier to flow of liquids.

To provide for more visually coherent designs, the first and second activated color regions can be within a CIELab color space volume of less than about 200. CIELab color space volume is discussed in more detail below. With such an approach, the colors of the activated color regions do not differ substantially to the eye of most viewers and viewers might perceive the colors to be shades or subtle variations of the same color. Subtle variations in color are thought to be pleasing to the eye, much like sample paint chips having slightly varying colors that can be pleasurable and interesting to view. If less distinctiveness between the first activated color region and second activated color region 70 is desired, activated color regions can be within a CIELab color space volume of less than about 50.

When the body facing surface 10 of the absorbent article 5 is viewed, the first activated color region 60 and second activated color region 70 are viewable by an observer. The first activated color region 60 and the second activated color region 70 are visibly distinct from the background region 50 in that the first activated colored region 60 and second activated color to region 70 each differ in color as compared to the background region 50. The first activated color region 60 and the background region 50 can differ in color by a ΔE, which is discussed in more detail below, of at least about 1, preferably at least about 3. Similarly, the second activated color region 70 and the background region 50 can differ in color by a ΔE of at least about 1, preferably at least about 3, so that the second activated color region 70 is noticeable against the background region 50.

The first activated color region 60 can be darker than the second activated color region 70. The darkness of a color can be quantified as L, discussed below, with lower values of L corresponding to darker colors. Such a design might be useful for situations in which the central portion of the absorbent article 5 has a greater fluid capacity than more peripherally located portions of the absorbent article 5. Further, a first activated color region 60 that is darker than the second activated color region 70 may provide for improved stain masking in the portion of the absorbent article 5 with which the first activated color region 60 is coordinated. It may not be desirable to mask a stain in the second activated color region 70 as much as in the central colored region 60 because if the wearer does not perceive the stain, she might not recognize that she should consider changing the absorbent article 5 in the near future.

Providing different colored regions on different layers of material of the absorbent article 5 can create a richer visual impression on the absorbent article 5. For instance, if the first activated color region 60 and second activated color region 70 are on different layers of materials, when viewed, at least one of the colored regions will be viewed through the layer comprising the other colored region. A colored region viewed through another layer material can have a significantly different visual impression in terms of softness/diffuseness of the image, somewhat like the difference between a matte finished photograph versus a gloss finished photograph or the way an undergarment looks beneath a sheer article of clothing. Further, if the first layer 20 and second layer 22 are different material types, for example one is a film and the other is a nonwoven, different activatable colorants or different concentrations of the same activatable colorant might be used on each layer. For instance, the activatable colorant material can be 'thermochromic', which means that the color change is induced by a change of temperature on one layer and 'photoreactive', which means that the color change is induced by light on the other layer. Alternatively, a top layer and lower layer may both contain photoreactive colorants, but the lower layer may have a higher concentration in order to achieve the same or darker color for color matching or depth perception, respectively.

Figure 2:
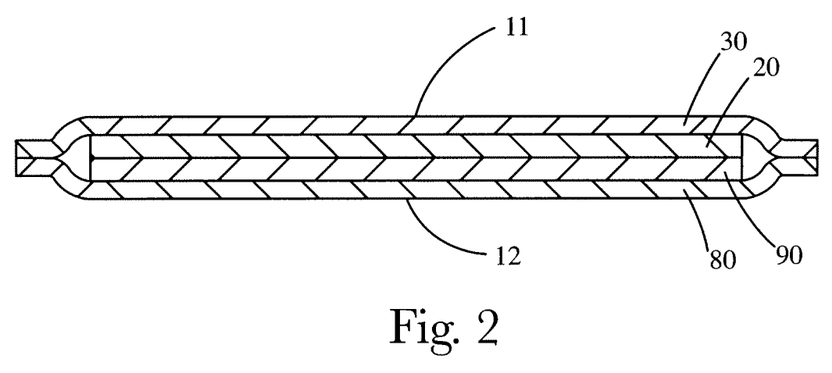
FIG. 2 is a cross-section of the absorbent article illustrated in FIG. 1.

A cross section of the absorbent article 5 illustrated in FIG. 1 is shown in FIG. 2. As illustrated, the absorbent article 5 can comprises a topsheet 30, a backsheet 80, and an absorbent core 90 disposed between the topsheet 30 and the backsheet 80. In some embodiments, each component of the absorbent article 5, and the absorbent article 5 itself, as illustrated in FIG. 2, can be considered to have a body facing side 11 and a garment facing side 12. The body facing side 11 is oriented towards the wearer's body or vaginal wall when the absorbent article is in-use and the garment facing side 12 opposes the body facing side 11. A tampon would not be considered to have a garment facing side since it is worn in the interior of the body.

Any of the first activated color region 60 or second activated color region 70 can be disposed on or be part of any layer of the absorbent article 5 so long as these colored regions are visually perceptible from the body facing side 11 of the absorbent article 5. These activated color regions can be located on, for example, the body facing side 11 or garment facing side 12 of any layer of the absorbent article 5. For instance, the first activated color region 60 can be disposed on the body facing side 11 of the absorbent core 90 and the second activated color region 70 can be disposed on the garment facing side 12 of the topsheet 30. Either of the first or second activated color regions can also be provided on an insert positioned between the topsheet 30 and the absorbent core 90.

To provide for more visually coherent designs, the first activated colored region 60 and second activated colored region 70 can be within a CIELab color space volume of less than about 200. CIELab color space volume is discussed in more detail below. With such an approach, the colors of the first activated colored region 60 and second activated colored region 70 do not differ substantially to the eye of most viewers and viewers might perceive the colors to be shades or subtle variations of the same color. Subtle variations in color are thought to be pleasing to the eye, much like sample paint chips having slightly varying colors found in home decoration stores that can be pleasurable and interesting to view. If less distinctiveness between the first activated colored region 60 and second activated colored region 70 is desired, the first activated colored region 60 and second activated colored region 70 can be within a CIELab color space volume of less than about 50.

The color of the first activated colored region 60 and second activated colored region 70 and background region 50 are measured by the reflectance spectrophotometer according to the colors L*, a*, and b* values. The L*, a*, and b* values are measured from the body facing surface 10 of the absorbent article 5 inboard of the periphery 110 of the absorbent article 5. The difference in color is calculated using the L*, a*, and b* values by the formula $\Delta E=[(L^*_X-L^*_Y)^2+(a^*_X-a^*_Y)^2+(b^*_X-b^*_Y)^2]^{1/2}$. Herein, the 'X' in the equation may represent the first activated colored region 60, the second activated colored region 70, or the background region 50 and 'Y' may represent the color of another region against which the color of such region is compared. X and Y should not be the same two points of measurement at the same time. In other words, for any particular comparison of the difference in color, the location of X does not equal ($\neq$) the location of Y.

Where more than two colors are used, the 'X' and 'Y' values alternately include points of measurement in them also. The key to the $\Delta E$ calculation herein is that the 'X' and 'Y' values should not stem from the same measured point on the viewing surface. In those instances where there is effectively no non-colored portion 50 within the confines of the measurement area, the 'X' values should flow from a point different in spatial relationship to the 'Y' values, but within the confines of the absorbent core periphery.

Reflectance color is measured using the Hunter Lab LabScan XE reflectance spectrophotometer obtained from Hunter Associates Laboratory of Reston, Va. An absorbent article 5 is tested at an ambient temperature between 65° F. and 75° F. and a relative humidity between 50% and 80%.

The spectrophotometer is set to the CIELab color scale and with a D50 illumination. The Observer is set at 10° and the Mode is set at 45/0°. Area View is set to 0.125" and Port Size is set to 0.20" for films; Area View is set to 1.00" and Port Size is set to 1.20" for nonwovens and other materials. The spectrophotometer is calibrated prior to sample analysis utilizing the black and white reference tiles supplied from the vendor with the instrument. Calibration is done according to the manufacturer's instructions as set forth in LabScan XE User's Manual, Manual Version 1.1, August 2001, A60-1010-862. If cleaning is required of the reference tiles or samples, only tissues that do not contain embossing, lotion, or brighteners should be used (e.g., PUFFS tissue). Any sample point on the absorbent article containing the activated color to be analyzed can be selected.

The absorbent article 5 is placed over the sample port of the spectrophotometer with a white tile placed behind the absorbent article 5. The absorbent article 5 is to be in a substantially flat condition and free of wrinkles.

The absorbent article 5 is removed and repositioned so that a minimum of six readings of color of the body facing surface 10 are conducted. If possible (e.g., the size of the activated color on the element in question does not limit the ability to have six discretely different, non-overlapping sample points), each of the readings is to be performed at a substantially different region on the externally visible surface so that no two sample points overlap. If the size of the activated colored region requires overlapping of sample points, only six samples should be taken with the sample points selected to minimize overlap between any two sample points. The readings are averaged to yield the reported L*, a*, and b* values for a specified color on an externally visible surface of an element.

In calculating the CIELab color space volume, V, maximum and minimum L*, a*, and b* values reported are determined for a particular set of regions to be measured. The maximum and minimum L*, a*, and b* values reported are used to calculate the CIELab color space volume, V according to the following formula:

$$V = \frac{4}{3}\left|\frac{\Delta L^*}{2}\right|\left|\frac{\Delta a^*}{2}\right|\left|\frac{\Delta b^*}{2}\right|$$

Within the above formula, $\Delta L^*$ is the difference in $L^*$ values between the two colored regions being compared and is calculated by: $\Delta L^* = L^*_X - L^*_Y$. The $\Delta a^*$ is the difference in $a^*$ values between the two colored regions being compared and is calculated by: $\Delta a^* = a^*_X - a^*_Y$. The $\Delta b^*$ is the difference in $b^*$ values between the two colored regions being compared and is calculated by: $\Delta b^* = b^*_X - b^*_Y$. The CIELab color space volume can result in a solid substantially ellipsoidal in shape. If $\Delta L^*$, $\Delta a^*$, and $\Delta b^*$ are equal, the solid will be spherical. As used herein, a "solid" refers to the mathematical concept of a three-dimensional figure having length, breadth, and height (or depth). An ellipsoidal volume is preferred to calculate volume because an ellipsoid generally requires the dimensional differences of $\Delta L^*$, $\Delta a^*$, and $\Delta b^*$ to be relatively more uniform than other solids. Furthermore, it is believed that ellipsoidal volumes are more visually acceptable (i.e., less detectable color mismatch by human perception) than spherical volumes.

In some embodiments, the activated colors of at least two externally visible surfaces of discrete elements will occupy a CIELab color space volume of less than about 200. The externally visible surfaces are analyzed according to the Test Method described below. Upon analysis, the inherent color of an element comprising an externally visible surface will yield $L^*$, $a^*$, and $b^*$ coordinates. The CIELab color space volume is then calculated using the formula presented above. The resulting volume can be less than about 200. The resulting volume can be less than about 50.

It should be recognized that the activated colors of more than two discrete colored regions may occupy the aforementioned CIELab color space volumes. In calculating the CIELab color space volume for more than two elements, the CIELab color space volume is calculated using the maximum and minimum $L^*$, $a^*$, and $b^*$ from a set of elements. The maximum color values and minimum color values are used to calculate V according to the formula presented above.

EXAMPLES

The following non-limiting examples are intended to illustrate potential embodiments of the present invention.

Example 1

A feminine hygiene pad is constructed comprising a film topsheet comprising a piezochromic colorant and a secondary topsheet comprising an airlaid material with a spunbond nonwoven carrier layer, wherein the nonwoven carrier layer comprises a photoreactive colorant. During the converting process, the secondary topsheet or sub-assembly of components including the secondary topsheet is exposed to UV light through a patterned screen in order to create a color pattern in a central zone of the secondary topsheet material. The product or sub-assembly is subsequently subjected to a bonding process which induces a color change in the film topsheet material in the pattern of the bond sites. Alternatively, the order of activation of the piezochromic colorant in the film topsheet and the photoreactive colorant in the secondary topsheet during the converting process can be reversed.

Example 2

A tampon comprising a nonwoven overwrap comprising a photoreactive colorant is inserted into a translucent plastic applicator comprising the same photoreactive colorant during the converting process. The tampon/applicator assembly is subsequently exposed to UV light through a patterned mask to create a color zone on both the applicator and the tampon. These color zones are perfectly registered with one another and work together to create and highlight a visual signal to the consumer of enhanced absorbency. Alternately, the overwrap and applicator may be activated separately and then combined.

Example 3

An absorbent article is constructed comprising a nonwoven topsheet and a nonwoven acquisition layer, each comprising the same or different photoreactive colorants. In a single activation step, the article is subjected to UV light, inducing color change in both the topsheet and the acquisition layer materials.

Example 4

An absorbent article is constructed comprising a nonwoven topsheet, a film backsheet and a foam core, each comprising a photoreactive colorant. During the converting process, the top surface of the article is exposed to UV light through a patterned mask to create patterns of color on both the topsheet and the top side of the core. Subsequently, the bottom surface of the article is exposed to UV light through a patterned mask to create a different pattern of color on the film backsheet and the bottom side of the core.

Example 5

A feminine hygiene pad comprising a photoreactive film backsheet and a film or nonwoven individual hygienic package release paper wrap (RPW) comprising photoreactive colorant is exposed to UV light through a patterned mask to create the same matching decorative pattern on both the RPW and the pad backsheet.

Example 6

An absorbent article is constructed comprising a nonwoven topsheet comprising a photoreactive colorant and an absorbent core containing fibers and/or Absorbent Gelling Material (AGM) comprising a photoreactive colorant. The absorbent article is exposed to UV light to create colored regions in the nonwoven topsheet and the absorbent core. The colored regions in the absorbent core correspond to areas of increased capacity for liquids.

Activation of the activatable colorant in the individual layers can be carried out in a variety of different ways. The external stimuli providing such color activation of the individual layers can be applied either sequentially or simultaneously during the converting process used in producing a disposable absorbent article. For example, a first layer may be unwound from a first supply roll and exposed to an external stimulus to induce color change and form a first activated color region. Separately, a second layer may be unwound from a second supply roll and exposed to an external stimulus to induce color change and produce a second activated color region. The first and second layers can then pass through a nip formed between a pair of calender rolls where the two layers are combined in overlapping manner.

Alternatively, the first and second layers can pass through the nip formed between the calender rolls, combined in an overlapping manner and then exposed to one or more external stimuli to induce color change in each of the constituent layers. For this embodiment, one external stimulus may induce color change in both layers simultaneously, or alternately, multiple external stimuli can be applied to separately induce color activation in each layer. For instance, in a configuration where the second layer overlaps the first layer, a first external stimulus can be applied through the second layer, activating the first activatable colorant in the first layer and not activating the second activatable colorant in the second layer. A second external stimulus can be applied to activate the second activatable colorant in the second layer.

In an alternate embodiment, color activation process comprises activating the first layer prior to combining it with the second layer, and then combining the first layer with the second layer. The second layer is activated via a second external stimulus after combining the second layer with the first layer. For this embodiment, the second external stimulus may or may not cause the activatable colorant in the first layer to undergo additional color change.

For each of the foregoing methods, the external stimulus required to activate the first and second activatable colorants in the first and second layers may be of the same or different type. For example the first external stimulus can be heat and the second external stimulus can be electromagnetic radiation such as UV light. Alternatively, both the first and second external stimulus may be electromagnetic radiation. For example, two UV light sources may be employed to activate the first and second activatable colorants in the first and second layers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or patent application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of producing color change in overlapping web layers comprising the steps of;
    a. providing a first web layer comprising a first activatable colorant;
    b. applying a first external stimulus to the first web layer to activate the first activatable colorant in the first web layer producing a first activated color region in the first web layer, wherein said first external stimulus comprises UV light;
    c. providing a second layer comprising a second activatable colorant wherein the second layer overlaps the first web layer;
    d. applying a second external stimulus to the overlapping layers to activate the second activatable colorant in the second layer producing a second activated color region in the second layer, wherein said second external stimulus comprises UV light.

2. The method of claim 1 wherein the first and second external stimuli are applied sequentially, one after another.

3. The method of claim 2 wherein the first external stimulus is applied through the second layer, activating the first activatable colorant in the first layer and not activating the second activatable colorant in the second layer.

4. The method of claim 1 wherein the first and second external stimuli are applied simultaneously, activating the first and second activatable colorants at the same time.

5. A method of producing color change in overlapping web layers comprising the steps of;
    a. providing a first web layer comprising a first activatable colorant;
    b. applying a first external stimulus to the first web layer to activate the first activatable colorant in the first web layer producing a first activated color region in the first web layer, wherein said first external stimulus comprises UV light;
    c. providing a second web layer comprising a second activatable colorant;
    d. applying a second external stimulus to the second web layer to activate the second activatable colorant in the second web layer producing a second activated color region in the second web layer, wherein said second external stimulus comprises UV light;
    e. conveying the first and second web layers in a machine direction; and
    f. combining the first and second web layers wherein the second web layer overlaps the first web layer.

6. The method of claim 1, wherein the first and second layers are selected from the group consisting of films, nonwovens, air laids, fibers, filaments, adhesives, lotions, absorbent gelling materials, and foams.

7. The method of claim 1 wherein the first and second layers form layers of an absorbent article selected from the group consisting of diapers, sanitary napkins, tampons, panty liners, incontinence devices, and wipes.

8. The method of claim 5 wherein the first and second external stimuli are applied sequentially, one after another.

9. The method of claim 5 wherein the first external stimulus is applied through the second layer, activating the first activatable colorant in the first layer and not activating the second activatable colorant in the second layer.

10. The method of claim 5 wherein the first and second external stimuli are applied simultaneously, activating the first and second activatable colorants at the same time.

11. The method of claim 5 wherein the first and second layers are selected from the group consisting of films, nonwovens, air laids, fibers, filaments, adhesives, lotions, absorbent gelling materials, and foams.

12. The method of claim 5 wherein the first and second layers form layers of an absorbent article selected from the group consisting of diapers, sanitary napkins, tampons, panty liners, incontinence devices, and wipes.

* * * * *